(12) United States Patent
Afsar et al.

(10) Patent No.: US 8,948,847 B2
(45) Date of Patent: Feb. 3, 2015

(54) MILLIMETER WAVE 3-D BREAST IMAGING

(71) Applicants: Mohammed N. Afsar, Somerville, MA (US); Liu Chao, Somerville, MA (US)

(72) Inventors: Mohammed N. Afsar, Somerville, MA (US); Liu Chao, Somerville, MA (US)

(73) Assignee: Tufts University, Medford, MA (US)

( * ) Notice: Subject to any disclaimer, the term of this patent is extended or adjusted under 35 U.S.C. 154(b) by 0 days.

(21) Appl. No.: 13/890,336

(22) Filed: May 9, 2013

(65) Prior Publication Data
US 2013/0303901 A1    Nov. 14, 2013

Related U.S. Application Data

(60) Provisional application No. 61/645,869, filed on May 11, 2012.

(51) Int. Cl.
*A61B 5/02* (2006.01)
*A61B 5/05* (2006.01)
*A61B 5/00* (2006.01)
*G06T 11/00* (2006.01)
*H01Q 13/02* (2006.01)
*H01Q 19/08* (2006.01)
*H01Q 19/12* (2006.01)
*H01Q 3/00* (2006.01)

(52) U.S. Cl.
CPC ............ *A61B 5/0507* (2013.01); *A61B 5/4312* (2013.01); *G06T 11/00* (2013.01); *H01Q 13/02* (2013.01); *H01Q 19/08* (2013.01); *H01Q 19/12* (2013.01); *H01Q 3/00* (2013.01)
USPC .......................................................... 600/430

(58) Field of Classification Search
USPC ......... 600/430, 407, 310, 473, 476, 438, 442, 600/2; 606/2, 12, 33; 128/915; 607/100, 607/101; 356/479
See application file for complete search history.

(56) References Cited

U.S. PATENT DOCUMENTS 5,807,257 A     9/1998  Bridges
2009/0185191 A1  7/2009  Boppart et al.

*Primary Examiner* — Michael Rozanski
(74) *Attorney, Agent, or Firm* — Chapin IP Law, LLC

(57) ABSTRACT

A system for imaging tissue includes a millimeter wave Quasi-optical backward wave oscillator. Tumorous tissue is detected in a reconstructed image using solvable inverse image reconstruction techniques. In one embodiment, three-dimensional breast imaging is enabled by providing radiation as a focused energy beam over a wide frequency range and at power levels to penetrate breast tissue disposed within dielectric compression plates.

20 Claims, 15 Drawing Sheets

MILLIMETER WAVE 3-D BREAST IMAGING

RELATED APPLICATIONS

This application claims the benefit of the filing date of earlier filed U.S. Provisional Patent Application having Ser. No. 61/645,869, filed May 11, 2012, and entitled "Millimeter Wave 3-D Breast Imaging," The entire teachings and contents of this Provisional Patent Applications is hereby incorporated by reference herein in their entirety.

BACKGROUND

To obtain a clear and thorough characterization of normal, benign, and malignant human tissues, it is important for one to use a technique that can yield highly accurate broadband dielectric data with the flexibility to accommodate different shapes, sizes, and composition of tissues. Millimeter waves provide great accuracy and resolution to obtain characteristics of tissues over a broad frequency range.

Conventional solutions to detecting tumors, for example techniques described in U.S. Pat. No. 5,807,257 using back scatter radar techniques have not proven successful because back scattering techniques often lead to ambiguous results and are computationally expensive in order to achieve high resolution images.

Numerous dielectric techniques have been developed for detection of cancerous tissues. Early studies of the electric properties of tissues and cells proposed a method of employing induced electric and magnetic currents on the surface of tissues to analyze resonance scattering and subsequently characterize tumors. However, this technique has severe limitations with sample size, orientation, and frequency. Pulsed microwave confocal systems for early breast cancer detection with few micro-calcifications have been proposed. Unfortunately, this technique exploits the significant water content and enhanced scattering that occurs in the microwave range, thus limiting its detection capabilities to the microwave range.

Much of the dielectric spectroscopy work in cancer detection has been conducted in the microwave range. Measurements of cancerous tissue up to 20 GHz using an open-ended coaxial probe have been obtained. The dielectric properties of materials have been characterized in the past by many methods. However, microwave dielectric spectroscopy has several disadvantages. Probe and sensor measurements are extremely sensitive to surface level modulations and external environmental conditions. Unless caution is exercised, inaccurate interface between the probe and sample can distort results. Microwave techniques are also roughly limited in the spectra with an upper limit of 30 GHz and lower limit of 300 MHz.

SUMMARY

While the penetration depth of such microwave signals is greater than millimeter and sub-millimeter wave signals, their resolution is much less. While microwave signals may be able to carry more power and detect tumors further below the tissue surface, they cannot obtain characteristics of tissues with greater accuracy and resolution than millimeter wave signals. A higher power higher resolution millimeter power source is necessary for significant depth of penetration. Higher power backward wave oscillators can provide higher power and stable millimeter wave matching this requirement. The Q-, V-, and W-bands free space quasi optical millimeter wave spectrometer energized by backward wave oscillators are utilized for the broad band measurements from 30 to 120 GHz. The typical tunable power level is about 20 to 40 milliwatts (mW) is adequate to show significant differences in transmittance for the normal and cancerous breast tissues.

It has been demonstrated, that tumorous tissue is around 10-40 times less transparent and higher absorbing in millimeter and THz waves than non-tumorous tissues. The unbalanced bridge approach can provide phase information which can help determine the dielectric permittivity. There is a great difference in dielectric properties between cancerous tissue and normal tissue in microwave frequencies. This anticipated difference in absorption levels and complex dielectric permittivity can be attributed to the large concentration of calcium deposits in tumors. In the millimeter-wave frequency range, tumorous tissues become almost nontransparent due to the enrichment of calcium in tissue cells. Furthermore, a possible explanation for the higher absorption levels in millimeter waves is that the backward-wave oscillator tubes generate significant amounts of continuous wave power compared to other techniques. This contrast in transmittance can derive complex permittivity with significant contrast.

In one embodiment, a technique for imaging tissue includes providing a quasi-optical millimeter wave spectrometer having a millimeter wave radiation from a backward-wave oscillator (BWO), modulating the radiation using a ferrite modulator, transforming the modulated radiation into a paraxial Gaussian beam, compressing the tissue between a pair of dielectric compression plates, transmitting the paraxial Gaussian beam through the compressed tissue and detecting tissue image amplitude and in phase data as a function of frequency. This technique provides directs radiation at relatively high power levels through a simple optical path normally incident on breast tissue which presents a flat surface by use of the dielectric compression plates. Such a technique reduces the scattering and return loss and therefore reduces the computational load during the imaging process because the radiation beam is normally incident to the entire surface of the breast thereby reducing reflection.

In a further embodiment the detected imaged data is processed using total variation regularization. In another embodiment Tikhonov regularization is used. In one embodiment, the millimeter wave radiation from the BWO is in a frequency range of approximately 30 GHz to approximately 120 GHz. In another embodiment the millimeter wave radiation from the BWO is in a frequency range of approximately 40 GHz to approximately 80 GHz. In a further embodiment the quasi-optical spectrometer is energized by tuning at least one BWO tube. In another embodiment the millimeter wave radiation from the BWO is in a power range of approximately 20 mW to approximately 40 mW.

In another embodiment a 3-D image is reconstructed and displayed. In yet another embodiment, a plurality of projections from different directions is generated and a three dimensional image of the tissue is rendered or reconstructed. In this embodiment, the pixels in the plurality of projections represent an accumulation of attenuation from the tissue. In a further embodiment, generating the plurality of projections includes determining a line integral of complex permittivity and repeating determining line integrals on parallel lines.

A exemplary system for imaging tissue includes a millimeter wave radiation source, a waveguide coupled to the radiation source, an isolator coupled to the waveguide, a modulator coupled to the isolator, a first antenna coupled to the modulator, a first focusing device coupling the radiation from the first antenna to a first compression plate and a second compression plate aligned with the first compression plate to form an aperture for receiving the tissue. Such a system is relatively easy to manufacture compared to conventional systems.

In further embodiment the system includes a second focusing device receiving radiation passing through the first and second compressing plates, a second antenna directing radiation from the second focusing device and a detector aligned to receive radiation directed from the second antenna. The first focusing device and the second focusing device can be lens assemblies or parabolic mirror assemblies.

In a still further embodiment the modulator includes a ferrite modulator and the millimeter wave radiation source comprises a backward-wave oscillator (BWO). In these embodiments, the BWO provides radiation over a frequency range of approximately 30 GHz to approximately 120 GHz and over a power range of approximately 20 mW to approximately 40 mW. In other embodiments the frequency range is approximately 40 GHz to approximately 80 GHz. In further embodiment the system includes an image processor using Total Variation regularization.

In further embodiment the system includes a rotation base disposed to rotate the millimeter wave radiation source, the waveguide, the isolator, the modulator, the horn antenna and the first focusing device around the first and second compression plates. In further embodiment the system includes a first directional coupler disposed between the modulator and the first antenna, a second directional coupler disposed between the second antenna and the detector and an attenuator disposed between the first directional coupler and the second directional coupler.

The inventors have observed that using advanced image techniques together with a high power BWO source, that 3-D breast millimeter wave imaging is possible. Embodiments described below exploit these electrical property contrasts in conjunction with a millimeter wave 3-D imaging system. Certain embodiments utilize these measurement techniques for millimeter wave for breast imaging in conjunction with translational/rotational stage which allows the variation of space or position of the sample. To achieve this higher resolution breast imaging, a set of linear equations are built to connect the different electrical properties of normal and cancerous tissues, variation of space and the reconstructed image over the frequency range. Subsequently, images of breast tissue structure are rendered.

A computer readable storage medium for tangibly storing thereon computer readable instructions includes instructions for providing a quasi-optical millimeter wave spectrometer having a millimeter wave radiation from a backward-wave oscillator (BWO), modulating the radiation using a ferrite modulator, transforming the modulated radiation into a paraxial Gaussian beam, compressing the tissue between a pair of dielectric compression plates, transmitting the paraxial Gaussian beam through the compressed tissue; and detecting tissue image amplitude and in phase data as a function of frequency.

Other arrangements of embodiments disclosed herein include software programs to perform the method embodiment steps and operations summarized above and disclosed in detail below. More particularly, a computer program product is one embodiment that has a computer-readable medium including computer program logic encoded thereon that when performed in a computerized device provides associated operations providing test systems explained herein. The computer program logic, when executed on at least one processor with a computing system, causes the processor to perform the operations (e.g., the methods) indicated herein as embodiments of the invention. Such arrangements of the invention are typically provided as software, code and/or other data structures arranged or encoded on a computer readable medium such as an optical medium (e.g., CD-ROM), floppy or hard disk or other media such as firmware or microcode in one or more ROM or RAM or PROM chips or as an Application Specific Integrated Circuit (ASIC) or as downloadable software images in one or more modules, shared libraries, etc. The software or firmware or other such configurations can be installed onto a computerized device to cause one or more processors in the computerized device to perform the techniques explained herein as embodiments of the invention. Software processes that operate in a collection of computerized devices, such as in a group of data communications devices or other entities can also provide the system of the invention. Embodiments of the system can be distributed between many software processes on several data communications devices, or all processes could run on a small set of dedicated computers or on one computer alone. It is to be understood that portions of the embodiments of the invention can be embodied, as software and hardware, or as hardware and/or circuitry alone

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Figure 1A:
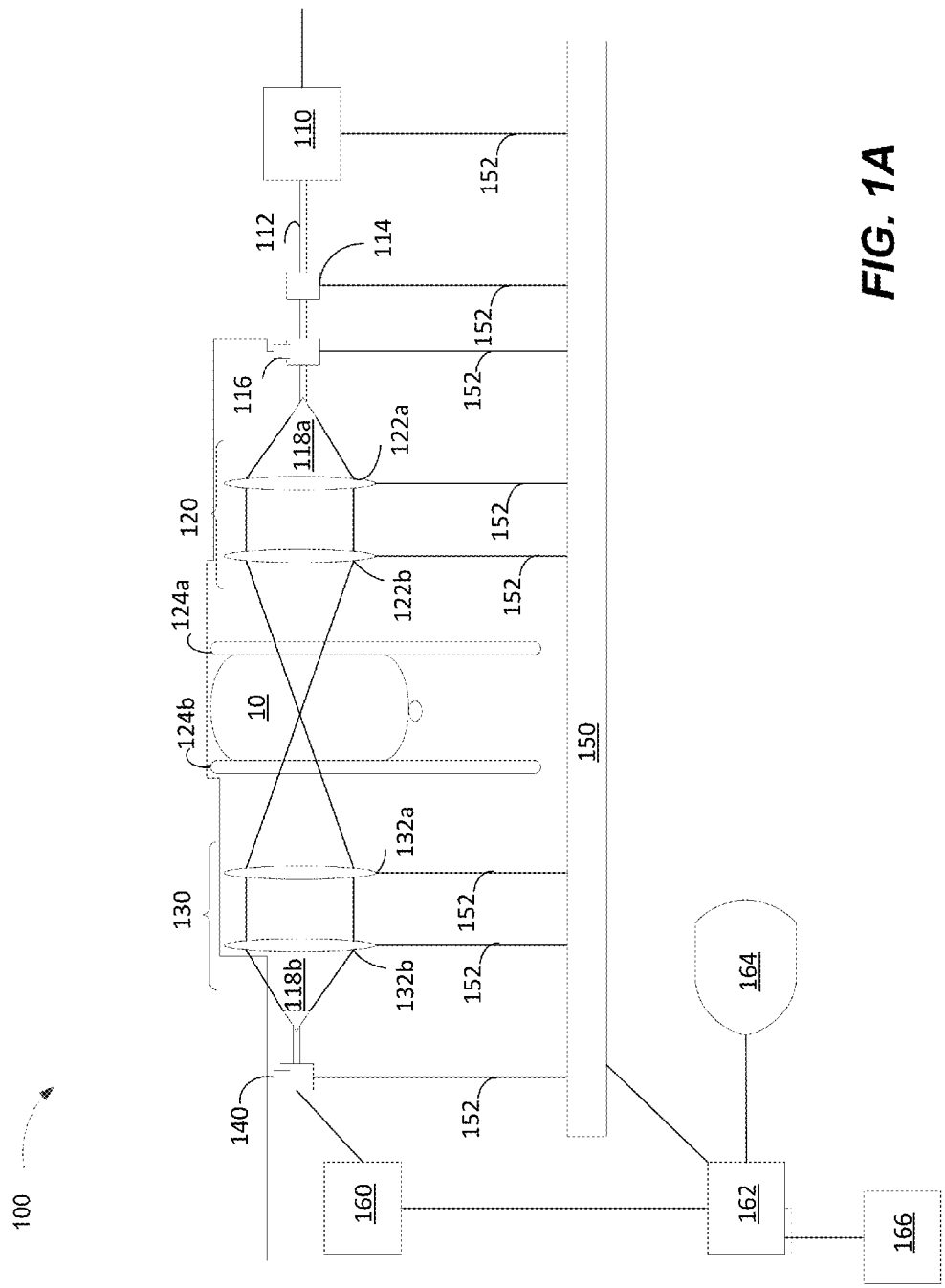
FIG. 1A is a schematic diagram of high power free-space quasi-optical millimeter wave biomedical imaging system including a waveguide, compression plates and a rotating base as disclosed herein.

The following examples and discussion illustrate various configurations of the disclosed approach. In the example configuration, the proposed approach facilitates imaging tissue using a millimeter wave biomedical imaging system. Now referring to FIG. 1A, a system for imaging tissue 100 includes a millimeter wave radiation source 110 producing radiation coupled through a waveguide 112 to an isolator 114. The system 100 further includes a modulator 116 coupled to the output of the isolator 114, and an antenna 118a coupled to the output of the modulator 116, a first focusing device 120 which focuses the output of the antenna 118a through a first compression plate 124a. Here, the first focusing device 120 includes a pair of lenses 122a and 122b. The system 100 further includes a second compression plate 124b which is aligned with the first compression plate and forms an aperture for receiving tissue 10 to be imaged. First and second compression plates 124a and 124b are collective referred to as compression plates 124. The combination of components (e.g., horn antennas and dielectric lenses) is referred to as a quasi-optical millimeter wave spectrometer.

The system 100 further includes a second focusing device 130 aligned with the first focusing device 120 to focus the millimeter radiation onto antenna 118b. Here, the second focusing device 130 includes a pair of lenses 132a and 132b. In one embodiment the lenses 122a, 122b, 132a and 132b are Teflon® lenses and the antennas 118a and 118b are horn antennas. The system 100 includes a detector 140 disposed to receive radiation from the antenna 118b. The system 100 also includes a rotational table 150 (lines 152 indicate which components are fixed relative to the rotational table 150). The system 100 also includes a controller 162 which is coupled to an image processing unit 160, a display 164, and a computer readable storage medium 166 and to the radiation source 110 and the modulator 116.

In one embodiment, the radiation source 110 is a high vacuum, high power, replaceable backward-wave oscillator (BWO), operating in Q-, V-, and W-bands: 30-120 GHz. The isolator 114 is a full band isolator, the antennas 118a and 118b are pyramidal horn antennas and the detector 140 is a Schottky diode detector. For highly absorbing specimens, the detector 140 is a specially designed liquid Helium cooled InSb detector would be utilized to enhance the measurement sensitivity. In one embodiment, the system uses multiple BWO oscillators (also referred to as BWO tubes). In this embodiment each individual BWO tube (vacuum tube) has a working frequency tuning range. In order to cover an entire frequency range (e.g., 30-120 GHz or 40-80 GHz), several BWO tubes are used.

In operation, the system 100 components are aligned. Millimeter energy is generated by the high power backward wave oscillator 110. The energy is sent by waveguide 112 to the isolator 114 which is used to protect the BWO source 110 from damage by any reflected energy. Modulation of the millimeter wave is accomplished by modulator 116. The modulated millimeter wave energy is transmitted through the first focusing device 120 and compression plates 124 and through the breast tissue 10 to reach the detector 140 at the end distal from the radiation source 110. Improved compression plates 124 are included in system 100. The compression plates 124 are located between the first and second focusing devices 120 and 130 and are used to compress the tissue 10 into a flat cylinder to present a flat surface to the energy beam (also referred to as radiation beam, beam, paraxial Gaussian beam or simply radiation). The reflection of the energy beam from horn antennas 118 is minimized by directing the beam at an angle normally incident to a flat surface of the compressed breast tissue. The normally incident angle generates lowest reflection from the breast tissue and dielectric compression plates 124. Energy is transmitted through the breast tissue 10 and reaches the detector 140.

During imaging operation, the frequency of the radiation source 110 is swept continuously at a step size as small as 6 MHz with average output power ranging accordingly from 10 mW to 25 mW in real-time to register high resolution interference patterns with relatively high power energy. The quasi-optical path, the radiation of BWO tube is modulated at frequency 3 kHz by a ferrite modulator. A specially fabricated pyramidal horn antenna transforms the obtained energy into the paraxial Gaussian beam. Four lenses along the wave propagation path from the source antenna to the receiver antenna control the diameter and the waists of the Gaussian beam. The specimen-under-test, prepared in a plane-parallel form, is placed in the central waist of the beam. The evaluation of dielectric and magnetic properties of a plane-parallel sample is performed by using the free space quasi-optical spectrometer in both transmittance and reflectance mode.

Figure 1B:
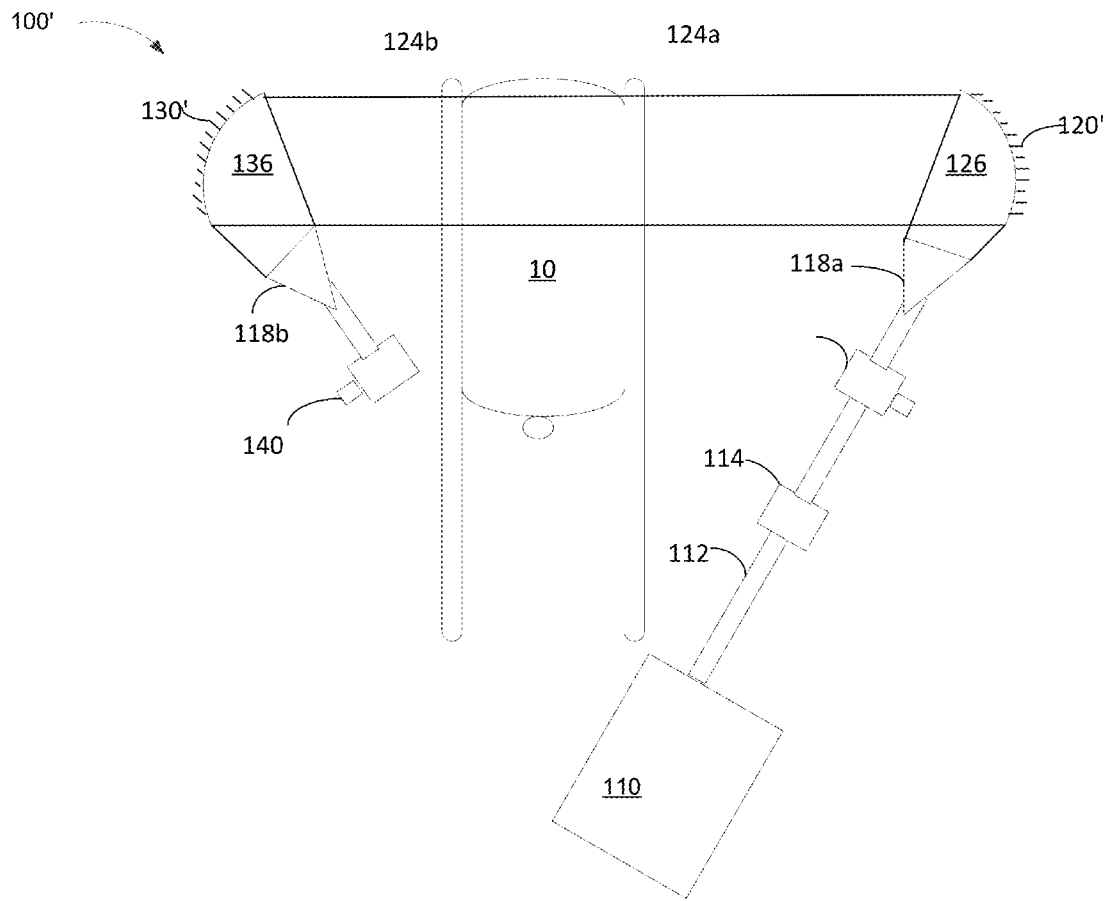
FIG. 1B is a schematic diagram of an alternate embodiment of FIG. 1 substituting parabolic mirrors as the focusing devices.
Figure 1C:
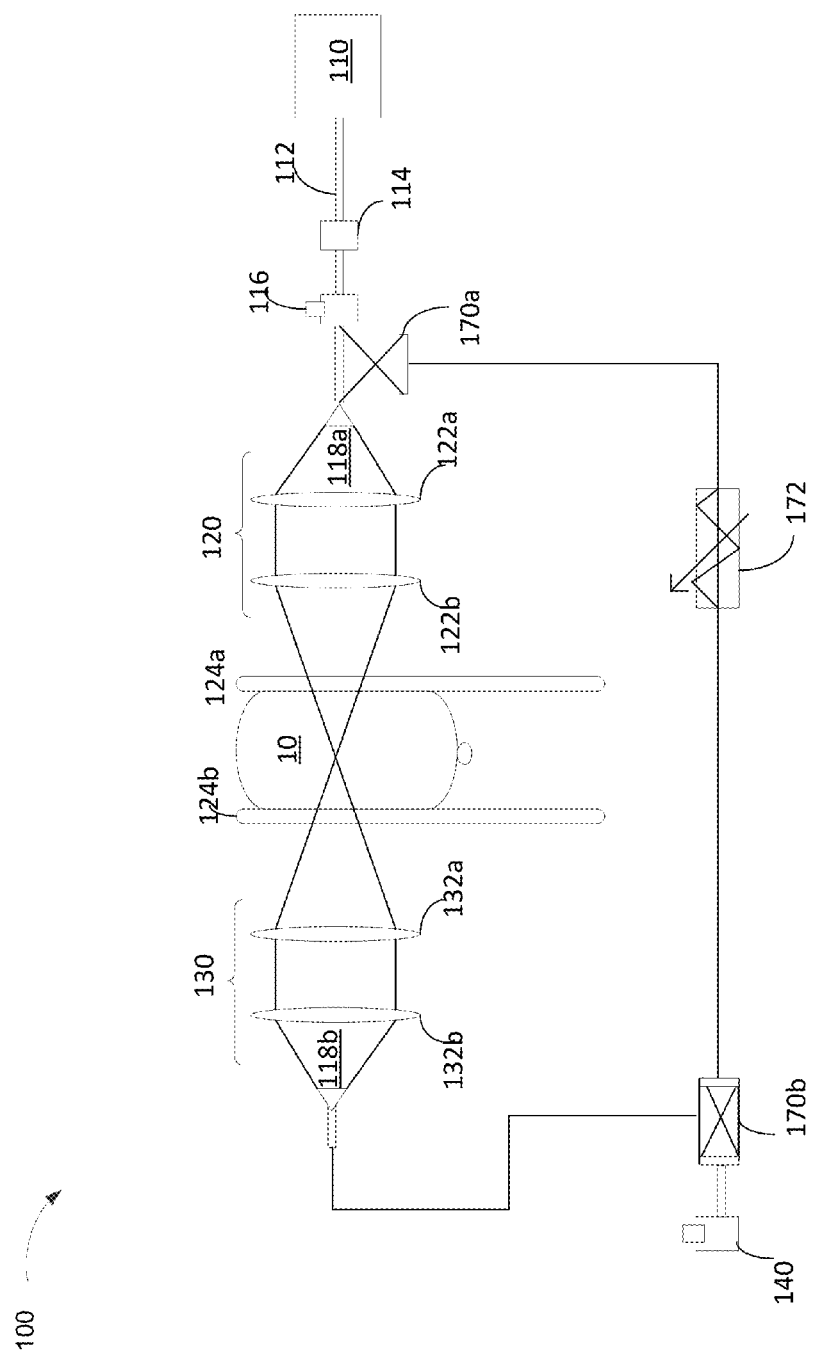
FIG. 1C is a schematic diagram of an alternate embodiment of FIG. 1A further including a directional coupler and a pair of attenuators.
Figure 1D:
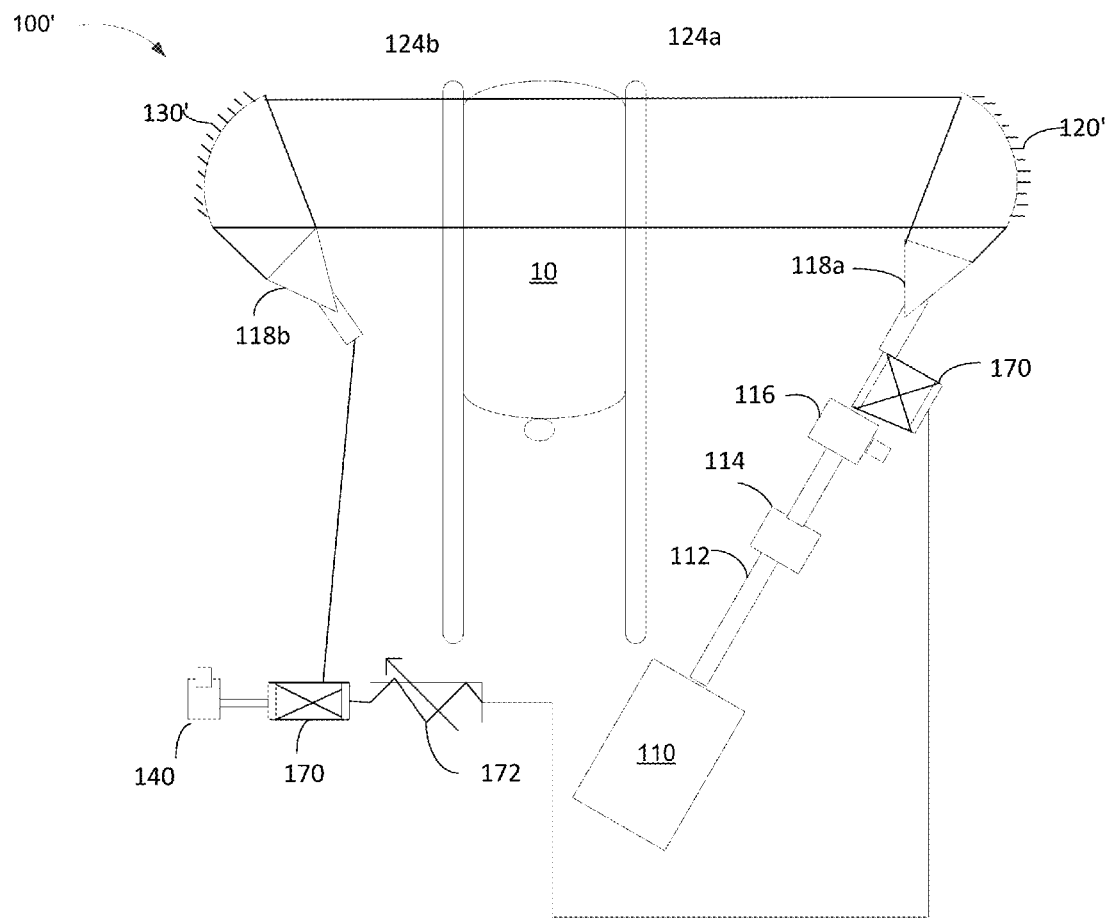
FIG. 1D is a schematic diagram of an alternate embodiment of FIG. 1B further including a directional coupler and a pair of attenuators.

FIGS. 1B-1D illustrate alternate embodiments of the millimeter wave tissue imaging system 100. Now referring to FIG. 1B, an alternative tissue imaging system 100' substitutes mirrors for the lenses in the first focusing device 120' and the second focusing device 130'. Here, the four Teflon lens 122a, 122b, 132a and 132b shown in FIG. 1A are replaced by two off-axis parabolic mirrors 126 and 136 to achieve a better effect on the millimeter wave energy beam because the parabolic mirrors have lower loss than dielectric lenses. Energy scattering from parabolic mirrors is also lower because in one embodiment the mirrors are fabricated as metallic mirrors. The position of the BWO source and the detector are modified and are no longer aligned in a straight line. The use of two parabolic mirrors 126 and 136 avoid the need to focus the divergent beam from the horn antenna 118a and into horn antenna 118b. The curvature of the parabolic mirror is designed match the geometry of the horn antennas 118a and 118b in order to form parallel beams. Using parallel beams avoids a requirement of adjusting the focal point of the lenses. Using parabolic mirrors 126 and 136 instead of lenses further reduces the loss of millimeter energy in the imaging system because the dielectric lenses do not have flat metallic surfaces and therefore incur dielectric losses and scattering losses at the surfaces of the lenses.

Now referring to FIG. 1C, system 100 can optionally include a first directional coupler 170a disposed between the modulator 116 and first antenna 118a, and a second directional coupler 170b disposed between the second antenna 118b and the detector 140. The system 100 also optionally includes an attenuator 172 disposed between the first directional coupler 170a and the second directional coupler 170b. The addition of these additional components forms an unbalanced bridge. The energy beam from BWO source 110 is divided at the first directional coupler 170a. The energy is directed to the attenuator 172 and recombines with the energy transmitted through the tissue 10 at the second directional coupler 170b. The combined energy is received by the detector 140. The unbalanced bridge provides two paths split by a directional coupler for the beam. One path without passing through tissue from the source to the detector serves as a reference. The other path is directed through the tissue with the same source and detector. Comparing the signal traveling through two paths, the amplitude and phase change will be known. The phase shift detection provides better imaging which can show the permittivity map of the tissue 10.

Now referring to FIG. 1D, a combination of the unbalanced bridge of FIG. 1C and the system 100' in FIG. 1B is shown. The system 100' with the unbalanced bridge achieves lower loss and more accurate imaging. It has all the advantages from the above system design. These embodiments use the millimeter wave radiation source 110 as a source of radiation for the Free Space Quasi Optical Spectrometer (i.e., horn antennas and dielectric lenses).

In operation in an embodiment for imaging breast tissue, the patient lies face down, placing the breast tissue between the compression plates. These embodiments use a quasi optical spectrometer and horn antenna, the energy beam is directionally oriented. The image processing algorithms differ from those used in conventional systems because the energy beam travels in known directions. As such, processor intensive Finite-Difference Time-Domain (FDTD) algorithms are not required. The compression plates 124 make the exposure area planar and parallel. The use of compression plates 124 facilitates the transmission of millimeter wave energy at desired angles for imaging. The compression plates 124 reduce the reflection of the electromagnetic energy. The distribution of the transmitter and receiver (source 110 and detector 140) are paired and disposed perpendicular to the compression plates. In certain embodiments, the components are placed under the rotating table 150 and move and rotate around the compression plates 124 enclosing breast area of the patient.

Figure 2:
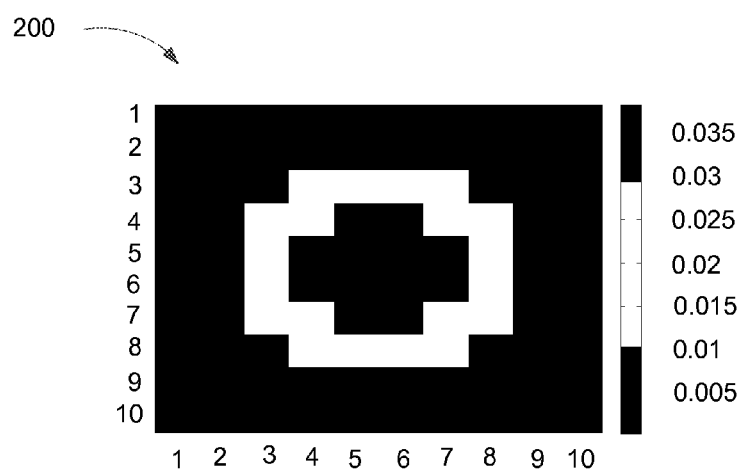
FIG. 2 is a diagram of a two-dimensional isotropic Gaussian energy beam distribution as generated by the system of FIG. 1A.

Now referring to FIG. 2, a two-dimensional isotropic Gaussian energy beam distribution used in tissue sample measurement is shown. The beam energy in the Quasi-optical BWO spectroscopy over a region follows a two-dimensional isotropic Gaussian distribution with zero mean and the standard deviation of σ.

$$f(x, y) = \frac{1}{2\pi\sigma^2}\exp\left(-\frac{x^2 y^2}{2\sigma^2}\right)$$

The following is the probability density function (p.d.f) $f(x,y)$ of the beam function.

From this p.d.f, the contribution of each pixel with respect to each measurement is obtained as follows:

$$V_{x,y} = \sum_{i=x-2}^{x+2} \sum_{j=y-2}^{y+2} \omega_{i,j} P_{i,j}$$

where V(x,y) is the measured value for each beam, P(i, j) is the true value for each pixel within the beam region and the weight for each pixel is defined as follows:

$$\omega_{i,j} = f(i-x, j-y) = \frac{1}{2\pi\sigma^2}\exp\left(-\frac{(i-x)^2(j-y)^2}{2\sigma^2}\right)$$

Figure 3:
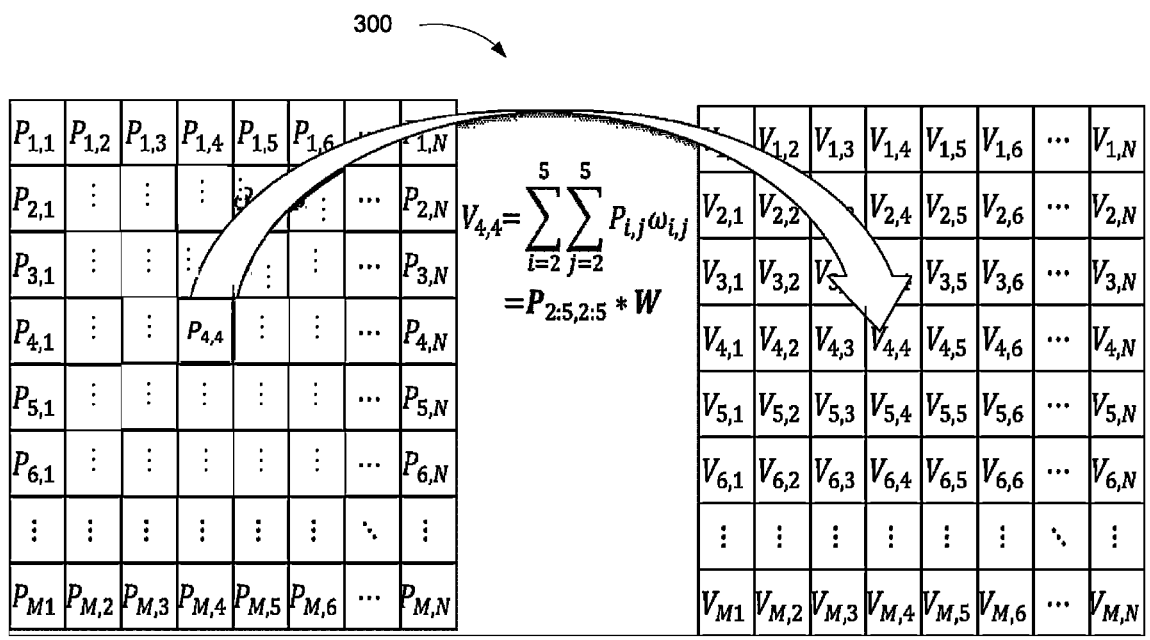
FIG. 3 shows a relation between the to be estimated and the measured values pixel values as collected by the system of FIG. 1A.

Since the weight function ω is isotropic, and then each measured value can be considered as the convolution result of the weight function ω and the region of true pixel values of the same size. FIG. 3 shows this process, where w is the kernel function of weights.

$$W = \begin{pmatrix} \omega_{1,1} & \omega_{1,2} & \cdots & \omega_{1,n} \\ \omega_{2,1} & \omega_{2,2} & \cdots & \omega_{2,n} \\ \vdots & \vdots & \ddots & \vdots \\ \omega_{n,1} & \omega_{n,2} & \cdots & \omega_{n,n} \end{pmatrix}$$

Now referring to FIG. 3 a schematic relationship 300 between the true pixel values and estimated and measured values is shown. Fast approximate solutions are found by using the Tikhonov algorithms with known kernel function as w. Exact solutions can be also found, if the measurement on the border takes $P_{x,y}$ outside of the region as zeros is considered. In such a method, M×N$V_{x,y}$ values establish M×N linear equations and thus can be solved exactly. The transformation for a specific pixel is shown.

Measurement and Reconstruction

The transmittance spectra of the entire normal tissue and entire carcinomas tissue are determined first. The measurements of transmittance spectra with entire normal and tumorous breast tissue samples are made from over approximate 40 GHz-80 GHz frequency range employing Quasi-optical Spectrometer energized by tunable BWO sources with 20 mW and 40 mW power levels. In another embodiment the frequency range is from about 30 GHz-120 GHz. In one experiment breast tissues were obtained from the Tufts—New England Medical Center (NEMC), Boston, Mass. The samples have been cut in the form of slices of 10×20 mm pieces and thickness of about 5 mm. The tissues were fixed and preserved in 10% formalin containers. In the measurement, pure normal and tumorous tissue samples have been placed in the specially made sample holder. The sample holder has been located at the focal spot between the two compression plates of quasi-optical free-space millimeter wave spectrometer. Data are acquired on the pure normal tissue and tumorous tissue at different power levels.

Figure 4:
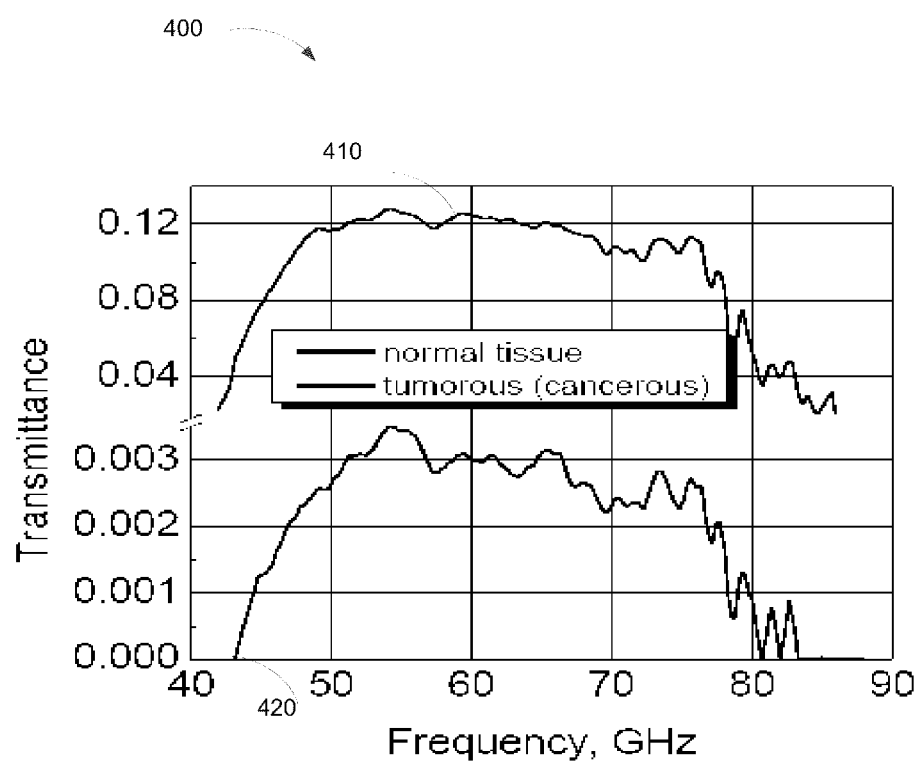
FIG. 4 shows the transmittance signal through non-tumorous (normal) and tumorous breast tissues as a function of frequency in millimeter waves as collected by the system of FIG. 1A.

FIG. 4 shows a graph 400 of the transmittance signal through non-tumorous, normal breast tissue 410 and tumorous breast tissue 420 as a function of frequency in millimeter waves. A comparison of transmittance spectra between different tissue and different source power indicates a significant difference in transmittance level of transmittance signals. For tumorous breast tissue transmittance level 420 is about 40 times lower than for the transmittance level of normal tissue 410. In one experiment, a plate scan was implemented to measure the sample. The diameter of the energy beam is about 5 mm. The samples are shifted 15 points from left to right and from top to bottom. Then the transmittance spectra at each sample point are converted to complex dielectric permittivity over the frequency range by following mathematical relationships:

The mathematical relationships between transmittance and reflectance spectra, and refractive and absorption index are shown below:

$$T = E\frac{(1-R)^2 + 4R\sin^2\psi}{(1-RE)^2 + 4RE\sin^2(\alpha+\psi)},$$

$$R = \frac{(n-1)^2 + k^2}{(n+1)^2 + k^2},$$

$$\varphi = \alpha + \arctan\frac{ER\sin^2(\alpha+\psi)}{1 - ER\cos^2(\alpha+\psi)} + \arctan\frac{k}{n^2 + k^2 + n} - \arctan\frac{k}{n+1},$$

$$E = e^{-4\pi k df/c},$$

$$\alpha = \frac{2\pi n df}{c},$$

$$n + ik = \sqrt{\varepsilon^*\mu^*},$$

$$\psi = \arctan\frac{2k}{n^2 + k^2 - 1},$$

where c, n, k, μ and ∈ are respectively the speed of light, refractive index, absorption index, permeability, and dielectric permittivity of the sample material; and T, R, φ, ψ are, respectively, the transmittance, reflectance, phase of the transmitted wave and reflected wave.

As long as the refractive and absorption index are available, the real and imaginary parts of permittivity can be obtained by using the following equations:

∈=∈'+i∈"

∈'=$n^2-k^2$

∈"=$2nk$ where n and k are refractive and absorption indices, respectively.

Figure 5:
FIG. 5 shows a blur projection of plate scanning result (left) and a restored tissue structure (right) of the sample as generated by the system of FIG. 1A.

A matrix of dielectric permittivity is generated by recording the permittivity at each sample point. Each element in this matrix is the projection of permittivity value over a large area on the sample. As the distance between neighboring sample points is much smaller than the beams diameter, the elements are overlapping each other. The map of the permittivity can be seen as blur spectrum. The image reconstruction method accompanied with the previous acquired normal tissue and tumorous transmittance spectra is applied to the linear equations. A clear and highly accurate tissue structure image is rendered (e.g., reconstructed). FIG. 5 shows an image reconstruction effect of the measurement of the sample. A blur projection of plate scanning result 510 and a restored tissue structure result 520 of the sample. The Normal tissue and the tumorous tissue can be distinguished easily. Each pixel in this image stands for 0.4×0.66 mm² size area. The sample includes primary breast carcinomas, fibroadenomas, and normal, nonneoplastic breast tissue. The grey level indicates the similarity to the entirely cancerous tissue in the previous measurement. The dark part is actually tumorous and brighter part includes normal tissue and fibroadenomas. The result shown here demonstrates the proof of concept of this millimeter wave imaging technique on ex-vivo tissue samples. Each this kind of image can be treated as a projection from a 3-D object.

Figure 6:
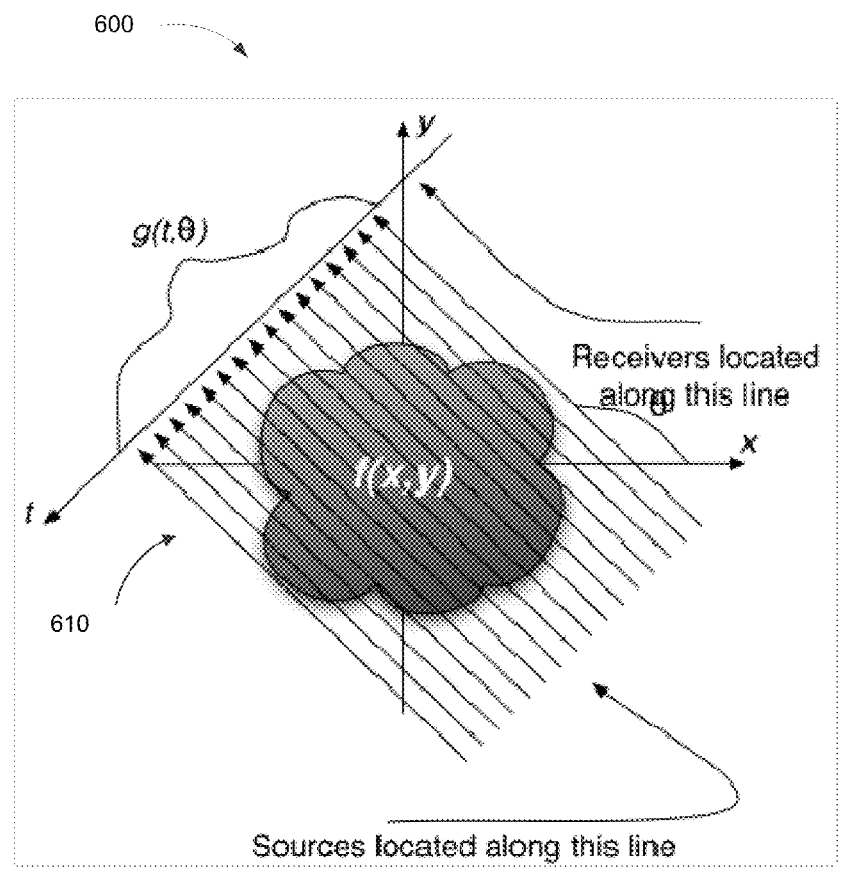
FIG. 6 is a schematic diagram of a parallel line millimeter wave beam scan as generated by the system of FIG. 1A.

Now referring to FIG. 6, three dimensional (3-D) reconstruction is described for a forward model used in an embodiment disclosed herein. If a plurality of projections from different directions are generated, a three dimensional image of the complete breast structure can be then rendered. Each pixel in the projection is an accumulation of attenuation from the tissue. The projection is then determined by a line integral of complex permittivity, which is assumed to follows a straight line, L, from the radiation source 110 to the detector 140. The linear attenuation function is denoted f, and is a function of the position (x,y,z) in a Cartesian coordinate system. If the intensity of the beam at a small cylinder with axis parallel with the beam propagating direction at position x is described by I(x), the loss of energy within a distance dl along the line L can be described as:

$$\frac{dI(x, y, z)}{I(x, y, z)} = -f(x, y, z) dl.$$

Since the intensity of the beam in the reference measurement without any sample, denoted as $I_r$, is known, the difference in intensity from where the beam is emerged to a point on the line L will be given as:

$$\int_L f(x, y, z) dl = \ln\left(\frac{I_r}{I}\right). \quad \text{[Equation 1]}$$

FIG. 6 shows a parallel line millimeter wave beam scan 600 to get projection in θ direction. The above described process is repeated on parallel lines 610 in FIG. 6. When actually doing a scan, there will be a finite number of lines corresponding to the number of source-receiver pairs. The configuration is rotated around the breast tissue 10, and a number of integrals as Equation 1 (above) are obtained. The inverse problem is to recover f(x,y,z) from these equations. Obtaining the integrals means that a face of the object has now been investigated in a certain direction θ. The integrals of a line t=x cos θ+y sin θ+z from the origin and direction θ is calculated, $$g(t,\theta,z) = \int_{-\infty}^{\infty} f(x,y,z)\delta(t-x\cos\theta - y\sin\theta - z)dxdydz.$$

In order to get the absorption function f(x,y,z) from the Radon projections, filtered back projection is employed. This includes of taking a Fourier transform and in the Fourier transform domain the frequency component (Jacobian determinant) |ω| is multiplied with projection g(t,θ,z). It is well known that due to ill-conditioned nature of the Radon operator, the high frequency noise in the raw data is amplified to unusable level. The inverse Fourier transform is made on a noisy signal with following form, g=R*f+noise, where R is the complete sample process and Fourier transform.

In order to deal with the noise, Tikhonov regularization is employed to reconstruct the projections ready for 3-D imaging which corresponds to the minimization of the following functional, $$\min(\|AX - Y\|^2 + \lambda\|X\|^2).$$

Figure 7:
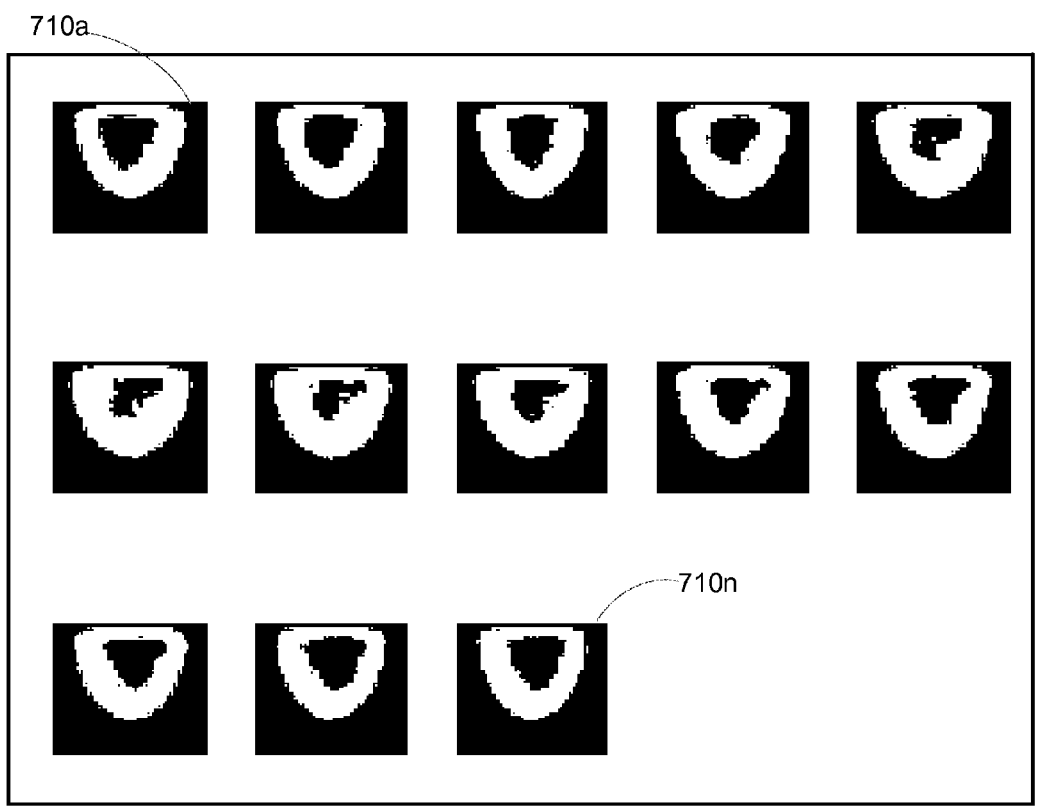
FIG. 7 shows noisy projections by a millimeter wave beam scan in 13 directions with a signal to noise ratio (SNR) equal to 30 dB as generated by the system of FIG. 1A.

FIG. 7 shows the noisy projections 710a-710n from the millimeter beam, here in thirteen directions. Here, the noisy projections 710a-710n have a signal to noise ratio (SNR) of approximately 30 dB. In FIGS. 7-10, tumors are indicated by black spots in the white areas of normal breast tissue.

Figure 8:
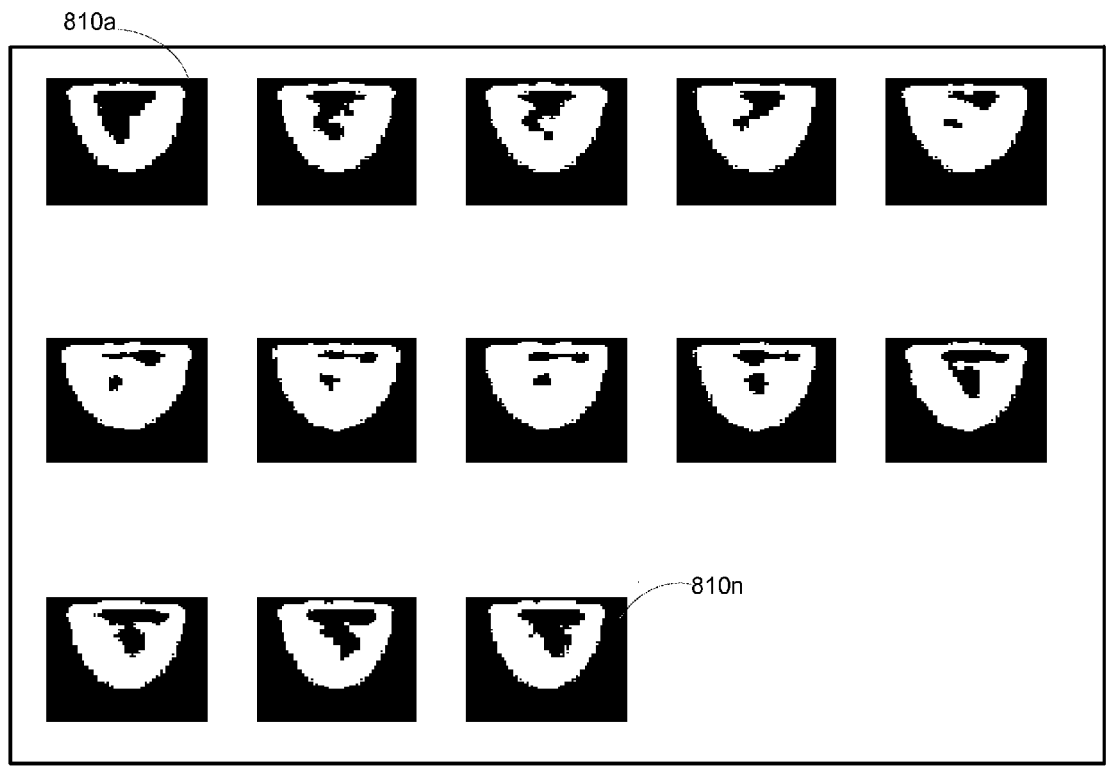
FIG. 8 shows reconstructed projections without nearby information from the millimeter wave beam using Tikhonov regularization according to embodiments disclosed herein.

FIG. 8 shows the reconstructed projections 710a-710n. The projections were reconstructed without nearby information from the millimeter wave beam using Tikhonov regularization with parameter λ equal to 0.01. These projections are used in the reconstruction of the corresponding 3-D breast image as described below using Total Variation Regularization. There are a finite number of projections from the object, and to reduce the scan time by the millimeter wave beam, fewer projections are generated. This reconstruction does not exploit the sparseness of the image for accurate reconstruction. So Total Variation (TV) penalization is employed in reconstruction using compressively sampled data. The high-resolution image of the breast under is reconstructed using limited Radon projections. The breast structure map can be acquired from the projections in this form:

$$f(x, y, z) = \frac{1}{(2\pi)^2} \int_0^\pi \int_{-\infty}^\infty \left( \int g(t, \theta, z) e^{-i\omega t} dt + \text{noise} \right) |\omega| e^{i\omega t} d\omega d\theta$$

Larger bandwidth can be obtained as the tissue is probed with higher frequencies. In other words, the ability to resolve high spatial frequency structure in an object requires correspondingly high temporal probing frequencies. This is definitely advantage of millimeter wave imaging over microwave. To reconstruct the 3-D breast image from this noisy, first-order method Total Variation regularization is then applied to these projections.

Let $\Psi = f(x,y,z)\delta(t - x \cos \theta - y \sin \theta - z)$, the Total Variation of the absorption coefficient of breast tissue $f(x,y,z)$ is defined as $$G(\Psi) = \int_\Omega \|\nabla \Psi\| dv, \ dv = dxdydz, v \in \Omega \subset R^2$$

The Euclidean norm is not squared, which means $g(\Psi)$ is non-differentiable. In order to handle this, a smoothed Total Variation functional is used namely Huber function, $$\phi_\tau(z) = \begin{cases} \|z\|_2 - \frac{1}{2}\tau & \text{if } \|z\|_2 > \tau, \\ \frac{1}{2\tau}\|z\|_2^2 & \text{else.} \end{cases}$$

Then, the approximated absorption coefficient functional is given by $$G_\tau(\Psi) = \int_\Omega \psi_\tau(\nabla \Psi) dv$$

Assume $\psi$ is discrete into $N = m \times m \times n$ array H, and let $h = \text{vec}(H)$. Each voxel of array H, with index $j$, has an associated discrete differential operator $D_j \in R^{3 \times N}$ such that the vector $D_j h \in R^3$ is the forward difference approximation of the gradient at $h_j$. By stacking all $D_j$ we obtain the matrix D of dimensions 3N by N:

$$D = \begin{pmatrix} D_1 \\ \vdots \\ D_N \end{pmatrix}$$

The gradient $\nabla G_\tau(\Psi) \in R^N$ of this function is $$\nabla G_\tau(\Psi) = \sum_{j=1}^N D_j^T D_j h / \max\{\tau, \|D_j h\|_2\}$$

The voxel value of absorption coefficient $f(x,y,z)$ in the reconstruction is in range of [0, 1]. Then the Total Variation regularization problem is described as $$\Psi = \text{argmin} \phi(\Psi),$$

$$\phi(\Psi) = \frac{1}{2}\|A\Psi - g\|_2^2 + \alpha G_\tau(\Psi),$$

where $\alpha > 0$ is the Total Variation parameter, which is solved to reconstruct the 3-D breast images.

Figure 9:
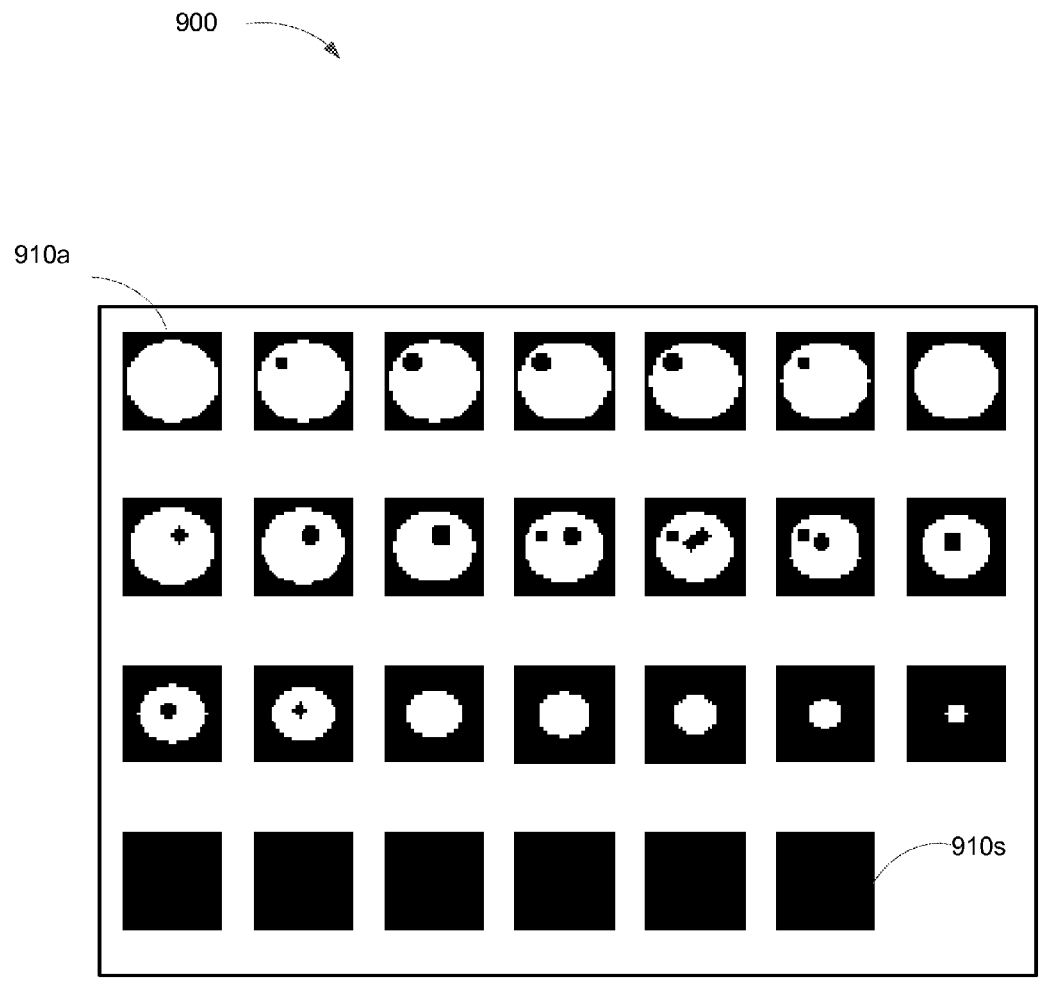
FIG. 9 is a three-dimensional (3-D) view of a simulated breast original simulative having several simulated tumors in layers.

FIG. 9 is a 3-D view 900 of simulated breast with fictitious tumors breast in layers 910a-910s. Here there are in 27 layers. By using the Total Variation regularization on raw data acquired, for example, by MATLAB software, the 3-D breast structure is reconstructed as shown in FIG. 10.

Figure 10:
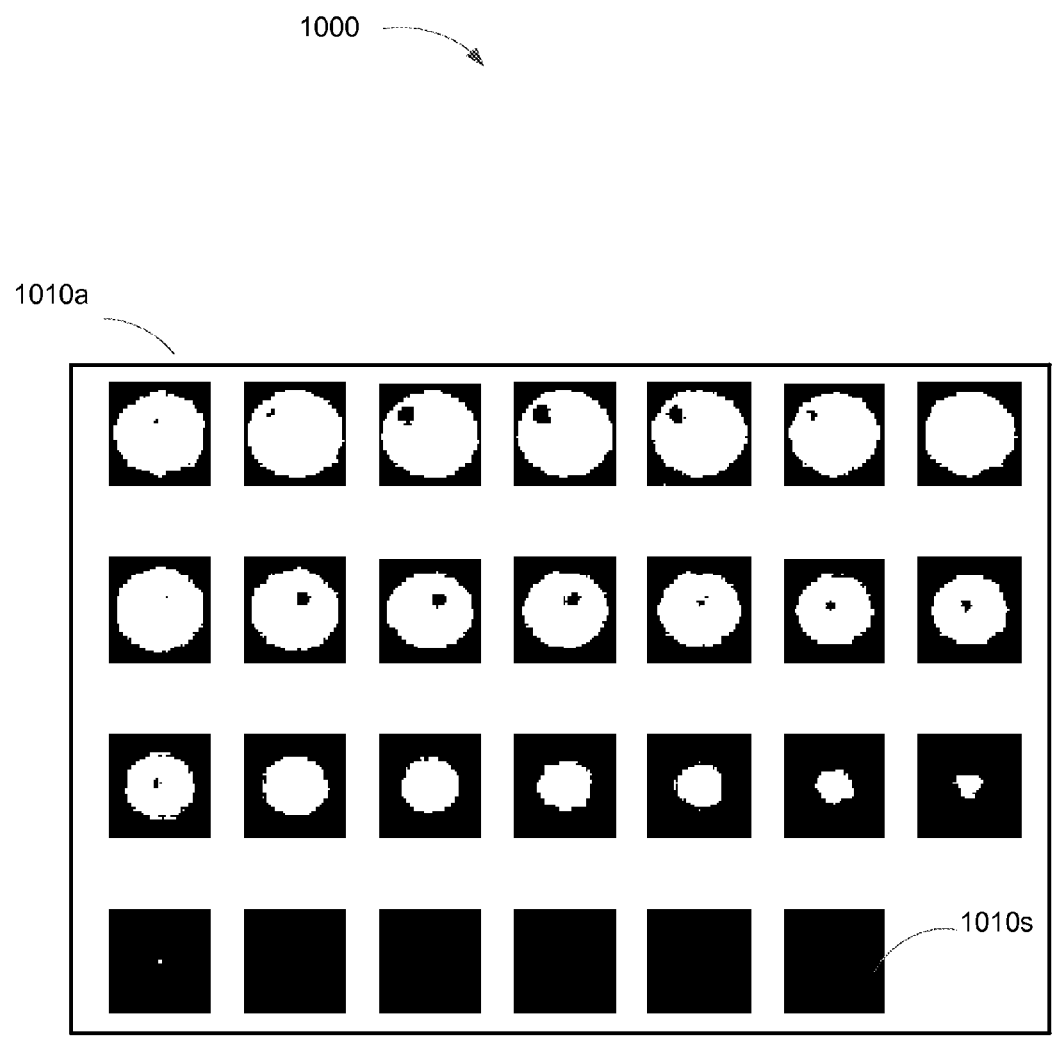
FIG. 10 shows reconstructed 3-D images by Total Variation regularization from 13 projections of breast tissue view in 5 layers.

FIG. 10 is a 3-D view 1000 of projections breast layers 1000a-1000s reconstructed by Total Variation regularization as described above.

Figure 11:
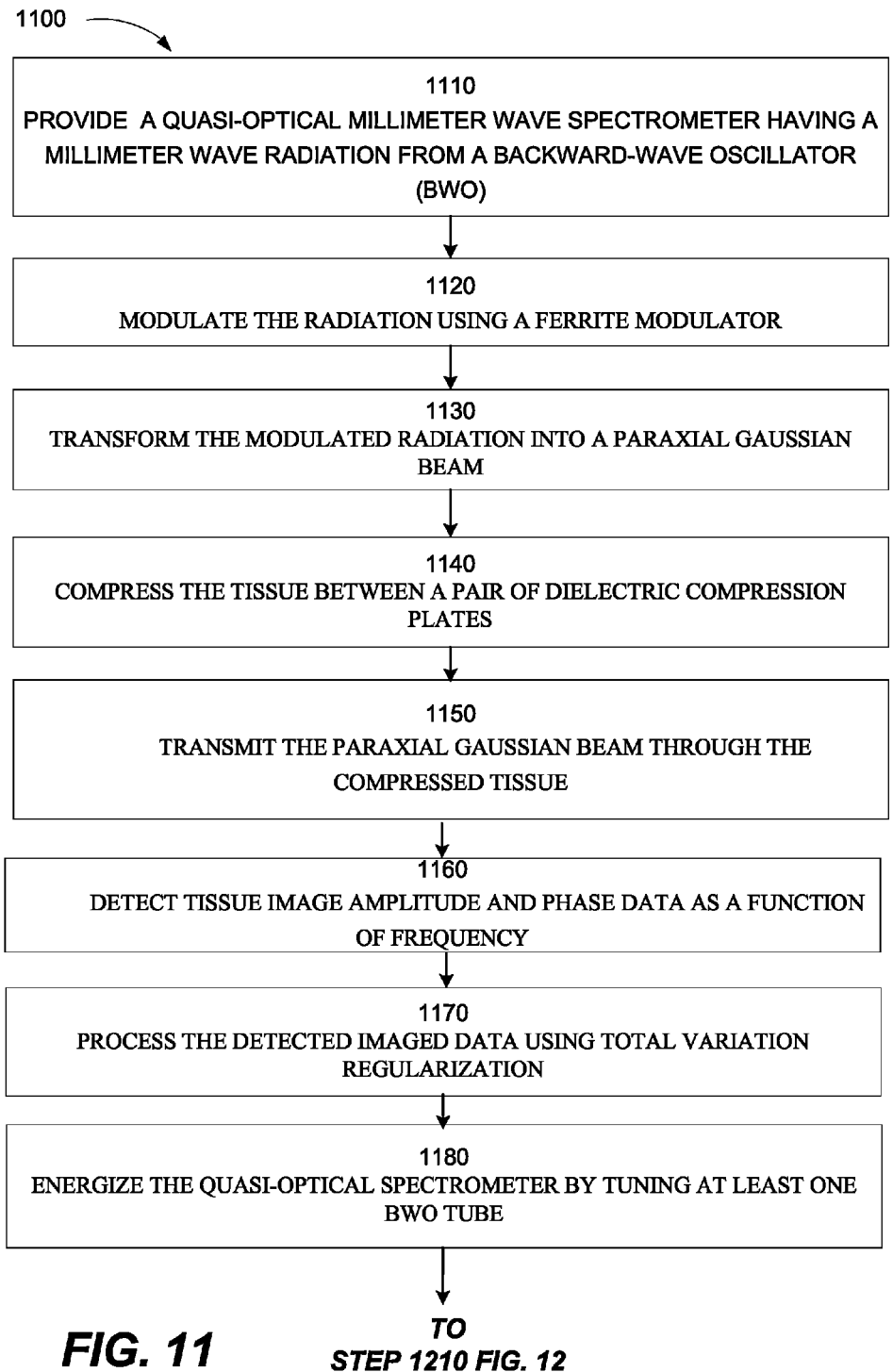
FIG. 11 is a flowchart of imaging tissue using the millimeter wave biomedical imaging system of FIG. 1A.

FIG. 11 shows a flowchart 1100 for imaging tissue using the system for imaging tissue 100 and the image processing unit 160 of FIG. 1. The imaging process begins by providing a quasi-optical millimeter wave spectrometer having a millimeter wave radiation from a backward-wave oscillator (BWO) at step 1110. The radiation is modulated in frequency using a ferrite modulator at step 1120. The modulated radiation is transformed into a paraxial Gaussian beam at step 1130. The tissue is compressed between a pair of compression plates at step 1140. The paraxial Gaussian beam is transmitted through the compressed tissue at step 1150 and detecting tissue image amplitude and phase data as a function of frequency at step 1160.

The imaging process continues at step 1170 where the detected imaged data is processed using total variation regularization at step 1170. In one embodiment Tikhonov regularization is used to process the data. In one embodiment, the millimeter wave radiation from the BWO is in a frequency range of approximately 30 GHz to approximately 120 GHz. In another embodiment the millimeter wave radiation from the BWO is in a frequency range of approximately 40 GHz to approximately 80 GHz. The quasi-optical spectrometer is energized by tuning at least one BWO tube at step 1180.

Figure 12:
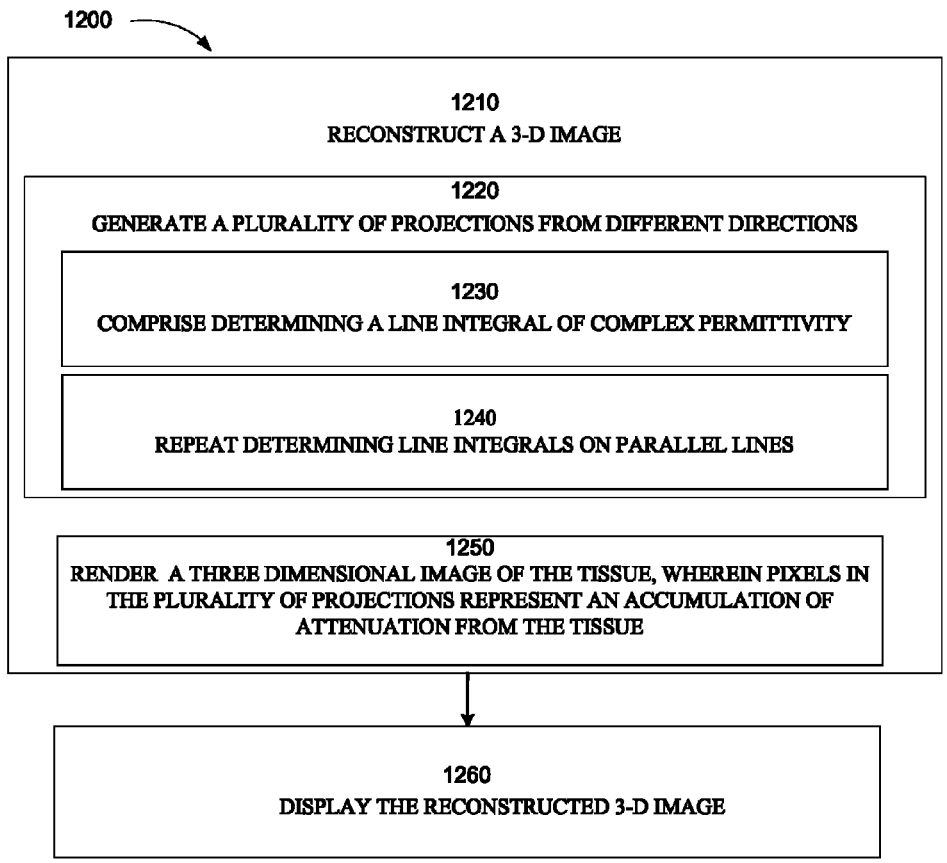
FIG. 12 is a flowchart showing further details of imaging tissue using the millimeter wave biomedical imaging system of FIG. 1A.

FIG. 12 shows a flowchart 1200 illustrating further detail of the process for imaging tissue. A 3-D image is rendered (i.e., reconstructed) at step 1210. A plurality of projections from different directions is generated at step 1220. A line integral of complex permittivity is determined at step 1230 and step 1230 is repeated at step 1240 to determine line integrals on parallel lines. A three dimensional image of the tissue is reconstructed by solvable inverse imaging reconstruction techniques (i.e., solving the inverse problems where many line integrals form a full projection of the breast in one direction). The inverse imaging reconstruction techniques utilizes the information from many spatial directions to recover the complex dielectric permittivity at each unit volume "which is one pixel") at step 1250. Rendering the 3-D images can include a variety of image processing techniques including digitally storing the image and conversion to 3-D. Pixels in the plurality of projections represent an accumulation of attenuation from the tissue. Finally the reconstructed 3-D image is displayed in step 1260.

The section headings used herein are for organizational purposes only and are not to be construed as limiting the subject matter described in any way. While the present invention has been described in conjunction with various embodiments and examples, it is not intended that the present teachings be limited to such embodiments or examples. On the contrary, the present invention encompasses various alternatives, modifications, and equivalents, as will be appreciated by those of skill in the art. While the teachings have been particularly shown and described with reference to specific illustrative embodiments, it should be understood that various changes in form and detail may be made without departing from the spirit and scope of the teachings. Therefore, all embodiments that come within the scope and spirit of the teachings, and equivalents thereto are claimed. The descriptions and diagrams of the methods of the present teachings should not be read as limited to the described order of elements unless stated to that effect.

The claims should not be read as limited to the described order or elements unless stated to that effect. It should be understood that various changes in form and detail may be made without departing from the scope of the appended claims. Therefore, all embodiments that come within the scope and spirit of the following claims and equivalents thereto are claimed.

The invention claimed is:

1. A method for imaging tissue comprising:
providing a quasi-optical millimeter wave spectrometer having millimeter wave radiation from a backward-wave oscillator (BWO);
modulating the radiation using a ferrite modulator;
transforming the modulated radiation into a paraxial Gaussian beam;
compressing the tissue between a pair of dielectric compression plates;
transmitting the paraxial Gaussian beam through the compressed tissue; and
detecting tissue image amplitude and phase data as a function of frequency.

2. The method of claim 1 further comprising processing the detected imaged data using total variation regularization.

3. The method of claim 2 wherein processing the detected imaged data using total variation regularization comprises using Tikhonov regularization.

4. The method of claim 1 wherein the millimeter wave radiation from the BWO is in a frequency range of approximately 30 GHz to approximately 120 GHz.

5. The method of claim 4 further comprising energizing the quasi-optical spectrometer by tuning at least one BWO tube.

6. The method of claim 4, wherein the millimeter wave radiation from the BWO is in a power range of approximately 20 mW to approximately 40 mW.

7. The method of claim 1 further comprising:
reconstructing a 3-D image; and
displaying the reconstructed 3-D image.

8. The method of claim 7, wherein reconstructing the 3-D image comprises:
generating a plurality of projections from different directions; and
rendering a three dimensional image of the tissue, wherein pixels in the plurality of projections represent an accumulation of attenuation from the tissue.

9. The method of claim 8, wherein generating the plurality of projections comprises determining a line integral of complex permittivity; and
repeating determining line integrals on parallel lines.

10. A system for imaging tissue comprising:
a millimeter wave radiation source;
a waveguide coupled to the radiation source;
an isolator coupled to the waveguide;
a modulator coupled to the isolator;
a first antenna coupled to the modulator;
a first focusing device coupling radiation from the first antenna to a first compression plate;
a second compression plate aligned with the first compression plate to form an aperture configured for receiving the tissue;
wherein the modulator comprises a ferrite modulator and the millimeter wave radiation source comprises a backward-wave oscillator (BWO); and
wherein the first antenna is configured for transforming millimeter wave radiation from the millimeter wave radiation source into a Gaussian beam.

11. The system of claim 10 further comprising:
a second focusing device receiving radiation passing through the first and second compression plates;
a second antenna directing radiation from the second focusing device; and
a detector aligned to receive radiation directed from the second antenna.

12. The system of claim 11, wherein the first focusing device and the second focusing device comprise lens assemblies.

13. The system of claim 11, wherein the first focusing device and the second focusing device comprise parabolic mirror assemblies and the first antenna comprises a horn antenna.

14. The system of claim 11 further comprising:
a first directional coupler disposed between the modulator and the first antenna; and
a second directional coupler disposed between the second antenna and the detector.

15. The system of claim 14 further comprising an attenuator disposed between the first directional coupler and the second directional coupler.

16. The system of claim 10, wherein the BWO provides radiation over a frequency range of approximately 30 GHz to approximately 120 GHz and over a power range of approximately 20 mW to approximately 40 mW.

17. The system of claim 10 further comprising an image processor using Total Variation regularization.

18. The system of claim 10 further comprising a rotating base disposed to rotate the millimeter wave radiation source, the waveguide, the isolator, the modulator, the antenna and the first focusing device around the first and second compression plates.

19. The system of claim 10, wherein the Gaussian beam is a paraxial Gaussian beam.

20. A non-transitory computer readable storage medium for tangibly storing thereon computer readable instructions for a method comprising:
providing a quasi-optical millimeter wave spectrometer having a millimeter wave radiation from a backward-wave oscillator (BWO);
modulating the radiation using a ferrite modulator;
transforming the modulated radiation into a paraxial Gaussian beam;
compressing tissue between a pair of dielectric compression plates;
transmitting the paraxial Gaussian beam through the compressed tissue; and
detecting tissue image amplitude and in phase data as a function of frequency.

* * * * *